(12) United States Patent
Hansen

(10) Patent No.: US 7,004,213 B2
(45) Date of Patent: Feb. 28, 2006

(54) DEVICE FOR DISTRIBUTING SUBSTANCES

(76) Inventor: Bernd Hansen, Heerstrasse 16, 74429 Sulzbach-Laufen (DE)

( * ) Notice: Subject to any disclaimer, the term of this patent is extended or adjusted under 35 U.S.C. 154(b) by 74 days.

(21) Appl. No.: 10/484,302

(22) PCT Filed: Jul. 15, 2002

(86) PCT No.: PCT/EP02/07850

§ 371 (c)(1),
(2), (4) Date: Jan. 20, 2004

(87) PCT Pub. No.: WO03/008021

PCT Pub. Date: Jan. 30, 2003

(65) Prior Publication Data

US 2004/0182471 A1    Sep. 23, 2004

(30) Foreign Application Priority Data

Jul. 17, 2001   (DE) .............................. 101 34 609

(51) Int. Cl.
*B65B 1/04* (2006.01)

(52) U.S. Cl. ..................... 141/329; 141/27; 604/192

(58) Field of Classification Search ............ 141/21–27, 141/329, 330; 604/192, 197, 198; 222/95, 222/96, 541.2–541.9
See application file for complete search history.

(56) References Cited

U.S. PATENT DOCUMENTS

| 4,139,009 A | | 2/1979 | Alvarez |
| 4,161,178 A | * | 7/1979 | Genese ....................... 604/413 |
| 4,735,618 A | | 4/1988 | Hagen |
| 5,836,922 A | | 11/1998 | Hansen et al. |

FOREIGN PATENT DOCUMENTS

WO    WO 99/51290    10/1999

* cited by examiner

*Primary Examiner*—Steven O. Douglas
(74) *Attorney, Agent, or Firm*—Roylance, Abrams, Berdo & Goodman, L.L.P.

(57) ABSTRACT

A device for distributing substances includes distribution container (1) receiving a substance. The container has a closing unit (3) provided with a canula (11) for the substance to be distributed. The outer end (15) of the canula protrudes from the closing unit (3). A safety device (5, 17) can alternate between a protective state in which it covers the outer end (15) of the canula (11), and a user state for the distribution of the substance from the canula (11).

6 Claims, 3 Drawing Sheets

DEVICE FOR DISTRIBUTING SUBSTANCES

FIELD OF THE INVENTION

The present invention relates to a device for distributing substances. A primary, but not exclusive, application of the device involves delivering a desired volume of a medium, especially a liquid medium, into a receptacle. Preferably, the medium to be delivered is an additive which is introduced, for example, as an admixture of an active ingredient into a fluid located in the receptacle. The receptacle can be an infusion container with contents with which the medium is to be admixed as an additional active ingredient.

BACKGROUND OF THE INVENTION

For this purpose, the delivery device is conventionally a syringe with a hypodermic needle which punctures the perforable closure or plug of the receptacle, for example, an infusion container. After puncture, by pressing the syringe, the medium is injected into the receptacle. In this process the preparatory working step of filling the syringe is necessary, in which the desired amount of the medium from a storage container is transferred into the syringe or the syringe is filled from a conventional vial which contains the measured dose of the pertinent medium. These working steps of transfer are on the one hand time-consuming, because the hypodermic needle and syringe must be unwrapped, the hypodermic needle mounted on the syringe, the vial opened or punctured and the syringe must be drawn up. On the other hand, in these measures, a major risk exists of contamination of the medium. Another problem in these delivery devices is the danger of injury to which the user is exposed during handling and which may be caused by the tip of the hypodermic needle. In this respect, a known delivery device, disclosed in U.S. Pat. No. 4,735,618, includes a safety device which has a safety body covering the end of the hypodermic needle and which can be moved from the effective protective state into the inactive state intended for delivery of the medium from the hypodermic needle. For this purpose, the safety body can be pushed along the hypodermic needle between an advanced protective position on the end of the hypodermic needle and the retracted state of use.

The disadvantage in this known device is that there are no provisions against unintentional movement into the position of use, in which the end of the hypodermic needle projects exposed. The known device can only be safeguarded after completed use by fitting the tip of the hypodermic needle in a receiving recess of the safety body after it has been advanced beyond the tip of the hypodermic needle after use of the device. The known device is therefore unsatisfactory from the standpoint of safety.

SUMMARY OF THE INVENTION

Objects of the present invention are to provide a device which offers increased safety against injuries during transport, storage and use.

These objects are basically achieved in the present invention by a delivery device which has a protective cover which can be removed from the delivery container and which encloses the end of the hypodermic needle. Not only is the danger of unintentionally pushing back the safety body of the safety device avoided, but in addition increased protection against contamination is achieved.

If the outer end of the hypodermic needle is designed to penetrate the perforable closure of the container which holds the medium which is to be delivered, when the closure is punctured the safety body can be pushed back by contact with it out of its advanced protective position on the end of the hypodermic needle into the position of use. After the hypodermic needle is pulled out of the closure, the safety body can be pushed forward again into the protective position. In this embodiment handling is especially simplified.

Preferably, the protective cover has a finger-grip knob as purchase for twisting the protective cover off of the delivery container.

As the safety body, the safety device can have an annular body movably guided on the section of the hypodermic needle projecting out of the closing unit. The annular body is connected to the closing unit by an elastic holding means which produces a holding force, is held by force-fit by the holding force of the holding means in the advanced protective position covering the end of the hypodermic needle, and can be pushed back against the holding force along the hypodermic needle into the position of use. The indicated annular body on its free face forms an annular broadened contact surface projecting on the forward point of the safety device radially over its other parts. By way of the widened contact surface, reliable contact behavior of the annular body with the puncturable point of the container on its removal opening results. Furthermore, as a result of the contact surface, when the perforable closure of the delivery container is punctured, the hypodermic needle cannot jam or be damaged on the sensitive tip.

The holding means can be formed by support elements which are divided by means of joints and which are articulated to the annular body and the closing unit, respectively. In the protective position, the support elements extend essentially parallel to the hypodermic needle. When the annular body is pushed back into the position of use along the hypodermic needle, the support elements extend in the position which is spread out from the hypodermic needle.

Preferably, the support elements are rod-like plastic parts, are molded in one piece to the closing unit, and are divided by bending joints at approximately half the length. In this execution, the inherent elasticity of the material of the support elements makes it possible for the annular body to be advanced automatically again at least partially against the front end of the hypodermic needle after being pushed back into the position of use, for the annular body therefore to return automatically back into the protective position, or after using the device for it to be advanced simply slightly farther forward. Since the bending joints can completely fold down laterally, the rod-like plastic parts which form the respective bending joint are placed in contact on top of one another so that a high penetration depth of the hypodermic needle into the delivery container can be achieved. Also perforable closures with the corresponding thicknesses of the delivery container can thus be punctured in a controlled manner by the hypodermic needle.

In one especially advantageous embodiment, the closing unit bears a snap ring which encloses the support elements and which can be removed from the closing unit and can be pushed along the support elements toward their bending joints to lock them in the position corresponding to the protective position. Catch notches can be provided on the bending joints into which the snap ring can snap so that the safety device is detachably locked in the protective position in which the annular body protectively encloses the outer end of the hypodermic needle.

The delivery container can be a plastic container produced using the known Bottelpack® process. The closing unit as an insert part is inserted into its open end before closing by means of the protective cover.

The body of the insert part in the central area contains the hypodermic needle which is located continuously in it. Its inner end projects slightly out of the body of the closing unit against the interior of the delivery container. The insert part, which forms the closing unit, has a membrane as a blocking element between the facing inner end of the hypodermic needle and the medium which is located in the delivery container. If the pressure of the medium which is located in the delivery container is increased, the blocking element is pressed against the end of the hypodermic needle and is punctured by it.

The increase of the pressure of the medium and the resulting puncturing of the membrane can be implemented by compressing the delivery container.

Other objects, advantages and salient features of the present invention will become apparent from the following detailed description, which, taken in conjunction with the annexed drawings, discloses a preferred embodiment of the present invention.

BRIEF DESCRIPTION OF THE DRAWINGS

Referring to the drawings which form a part of this disclosure.

DETAILED DESCRIPTION OF THE INVENTION

Figure 3:
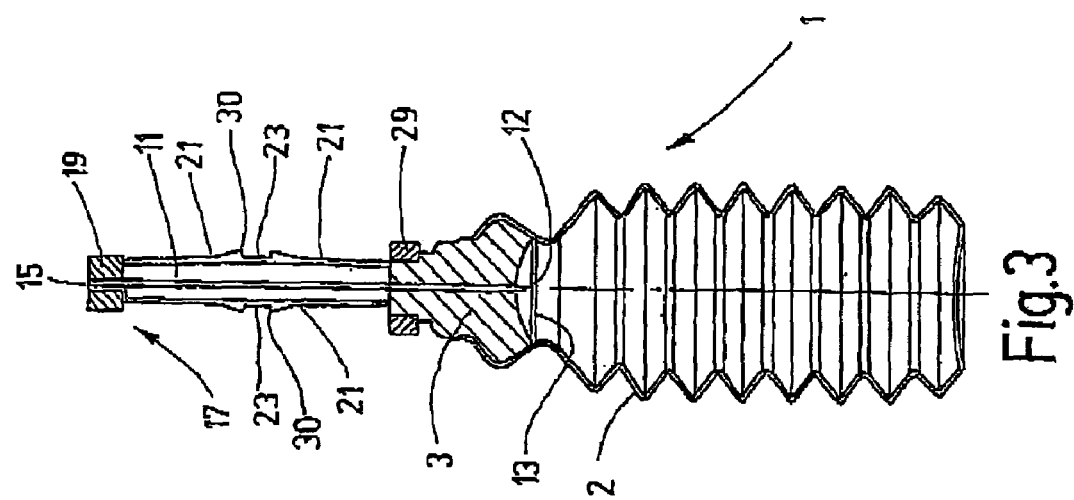
FIG. 3 is a side elevational view in section of the device of FIG. 1, but with the protective cover removed.
Figure 1:
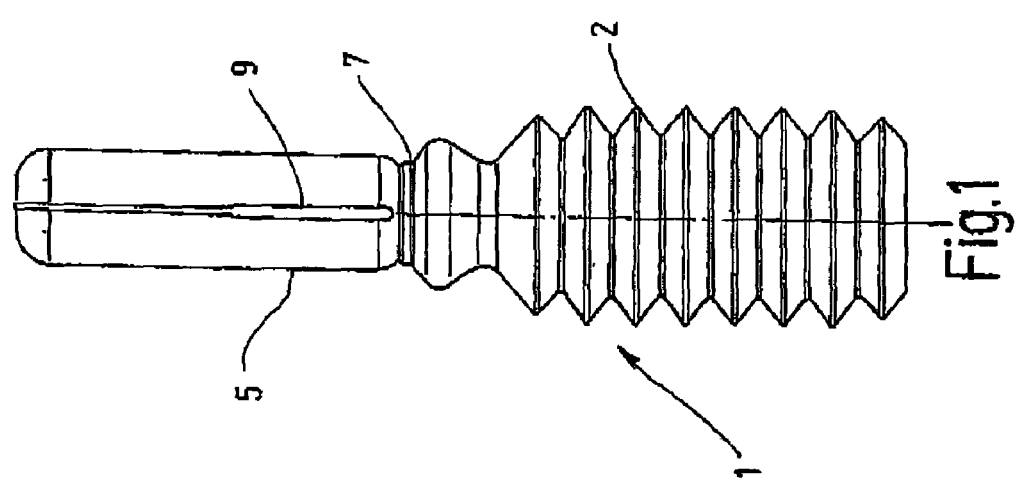
FIG. 1 is a side elevation view of a delivery device according to an embodiment of the present invention in an operating state before use, i.e., with the protective cover mounted.

In the drawings, the delivery container is designated as a whole as 1. It is an ampule-like plastic container which has been produced using the known Bottelpack® process. The delivery container has a wall 2 provided with folds and made bellows-like, so that the delivery container 1 can be squeezed out from the configuration shown in FIGS. 1 to 4 to that shown in FIGS. 5 to 7. In the neck area, a closing unit 3 is inserted into the delivery container 1 as an insert part. Several components are molded onto the body of the closing unit which is molded from plastic. Among others, a safety device 17 is provided, which, before using the delivery device, is protected by a protective cover 5 molded on at a predetermined breakage point 7, see FIGS. 1 and 3, to the body of the delivery container 1. The cover has a laterally projecting finger-grip knob 9 which is used as purchase to twist the protective cover 5 off the delivery container 1 at the predetermined breakage point 7. FIG. 3 shows the same operating state of the device as FIGS. 1 and 2, but with the protective cover 5 removed.

Figure 2:
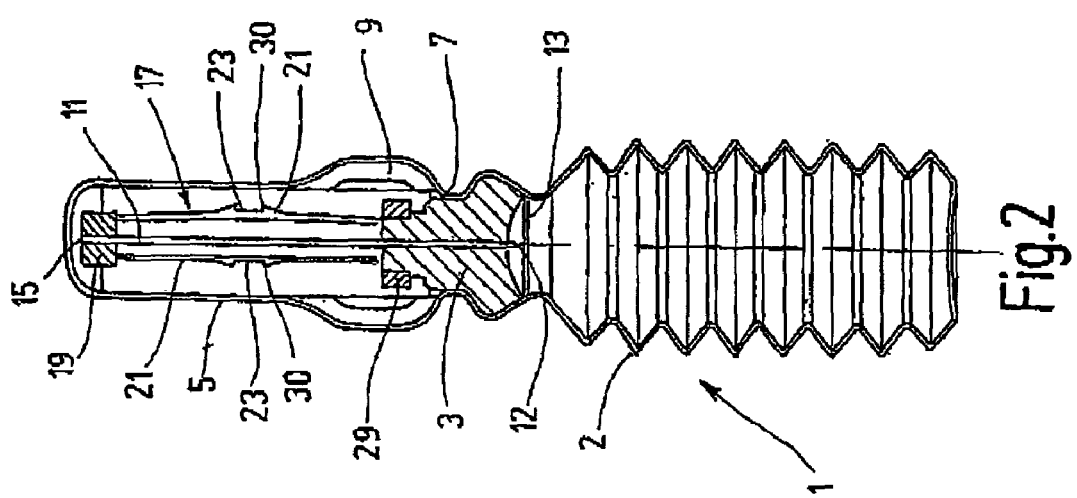
FIG. 2 is a side elevational view in section of the device of FIG. 1.

As is especially apparent from FIGS. 2 and 3, the body of the closing unit 3 in the central area is penetrated by the hypodermic 11 needle. The needle inner end 12 projects slightly to the inside of the delivery container from the body of the closing unit 3. Between the inner end 12 of the hypodermic needle 11 and the interior of the delivery container 1, there is a membrane 13 which is part of the insert part of the closing unit 3.

Figure 7:
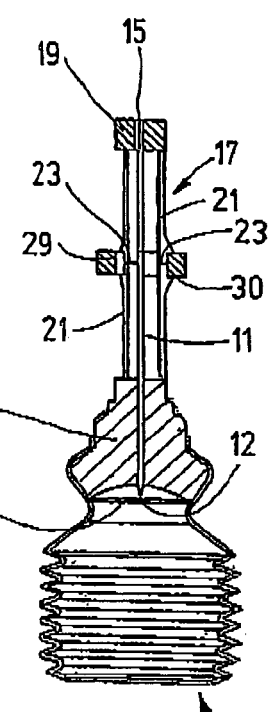
FIG. 7 is a side elevational view in section of the device of FIG. 1 in an operating state where the delivery container has been squeezed out and which corresponds to the protective position of the safety device.

The hypodermic needle extends from the outer end of the body of the closing unit 3 to a length which corresponds approximately to the length of the syringe hypodermic needle. FIGS. 2, 3, and 7 show operating states in which the projecting outer end 15 of the hypodermic 11 needle is covered, i.e., protected, by safety device 17 which is in its protective position.

The safety device 17 is molded in one piece to the body of the closing unit 3 and has an annular body 19 which can be moved on the hypodermic needle 11 and is located in the protective position (see FIGS. 2, 3, and 7) on the outer end 15 of the hypodermic needle 11 to cover this end of the hypodermic needle, i.e., the tip of the needle. The annular body 19 is connected in one piece to the body of the closing unit 3 by support elements 21 of a rod-like shape which are molded on in one piece. The connecting points of the support elements to the annular body 19 and the body of the closing unit 3 are flexible in the manner of bending joints. In addition, at approximately half of the length of the support elements 21, bending joints divide the support elements 21. If the annular body 19 is pushed out of the protective position into the position of use of the device along the hypodermic needle 11, see FIGS. 5 and 6, the sections of the support elements 21 bordering the bending joints 23 swivel so that they are spread out from the hypodermic needle 11 and are folded as is shown in FIG. 5.

Figure 4:
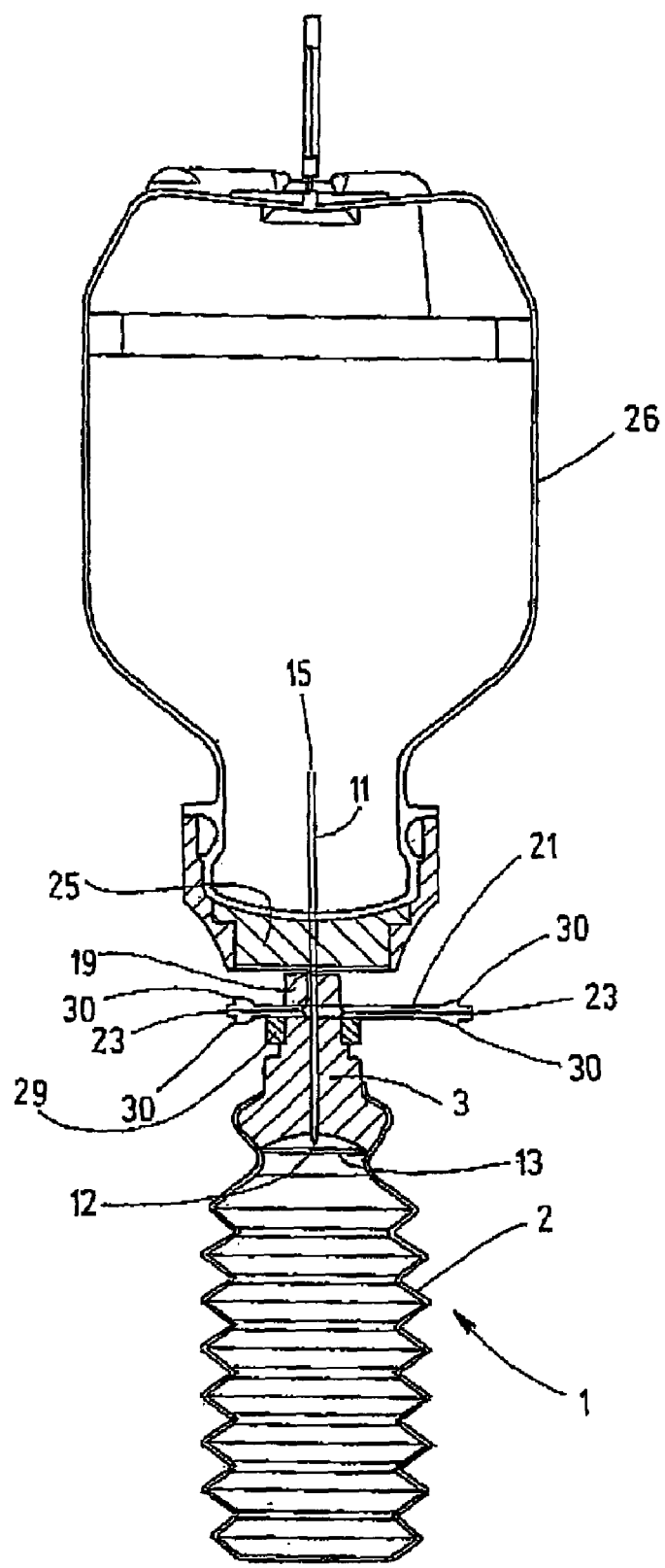
FIG. 4 is a side elevational view in section of the device of FIG. 1 in an operating state where the device has been pushed into the perforable closure stopper of an infusion container.
Figure 5:
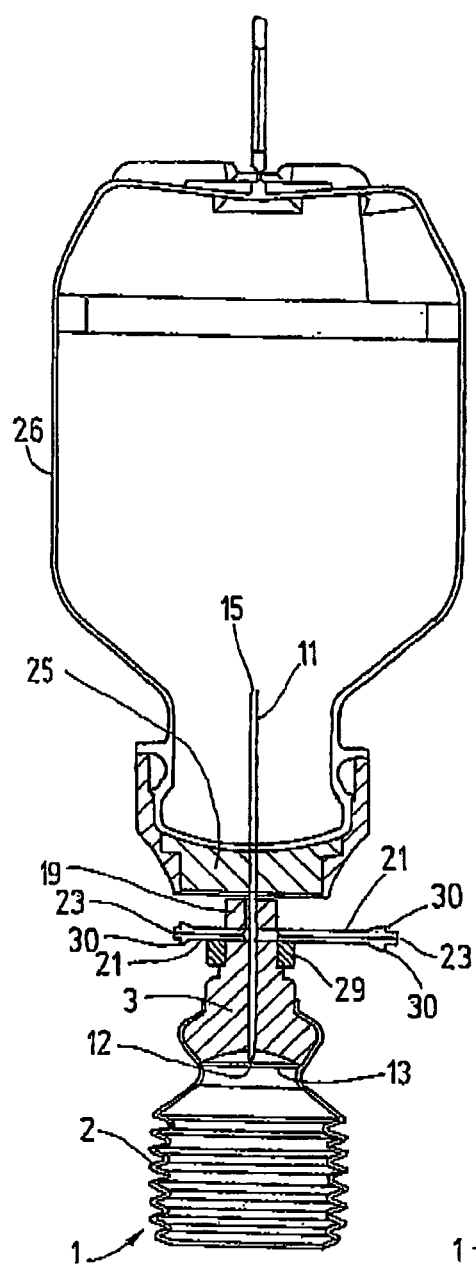
FIG. 5 is a side elevational view in section of the device of FIG. 1 in an operating state where the delivery container of the device is being squeezed out.

FIG. 5 and FIG. 4 show the device in the state in which the hypodermic needle 11 with its front end 15 has punctured the perforable closure 25 of an infusion container 26. Here, the annular body 19 is pushed back into the position of use along the hypodermic needle 11 out of the protective position aligned with the outer end 15 of the hypodermic needle. By compressing the bellows-like wall 2 of the delivery container 1 (see FIG. 5), the pressure of the medium it contains is increased so that the membrane 13 is pressed against the facing inner end 12 of the hypodermic needle 11 and is punctured by it. Compressing the delivery container 1 further leads to the medium contained in it being squeezed out into the infusion container 26 so that a dose of an additive or active ingredient which corresponds to the contents of the delivery container 1 is added to the contents of the infusion container 26.

Figure 6:
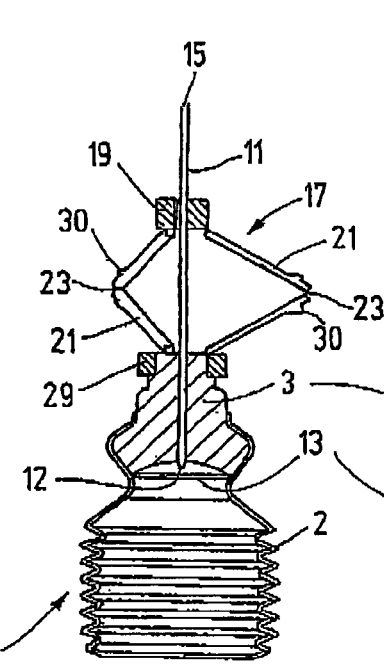
FIG. 6 is a side elevational view in section of the device of FIG. 1 in an operating state where the delivery container has been squeezed out and withdrawn from the closure stopper.

FIG. 6 shows the operating state after the delivery container 1 has been squeezed out and is withdrawn again from the closure 25 of the infusion container 26. As a result of the inherent elasticity of the support elements 21, the annular body 19, which had been pushed back beforehand out of the protective position when the hypodermic needle is inserted into the closure 25 by contact therewith against the elasticity or holding force of the support elements 21, is automatically advanced again by the force of elasticity in part against the end 15 of the hypodermic needle.

FIG. 7 shows the operating state of the device after its completed use. The projecting outer end 15 of the hypodermic needle 11 is secured again by the safety device 17, although the protective cover 5 is no longer mounted. For this purpose, a snap ring 29 sits removably on the body of the closing unit 3, is removed from the closing unit, and is advanced along the hypodermic needle 11. Sliding the snap ring over the support elements 21 brings them out of the position shown in FIG. 6 to the hypodermic needle 11, with the annular body 19 being advanced as far as the end 15 of the hypodermic needle 11. On the bending joints 23 the support elements 21 have molded catch notches 30 into which the snap ring 29 fits (see FIG. 7).

After the snap ring 29 catches in the catch notches 30 on the bending joints 23 of the support elements 21, the hypodermic needle 11 is covered by the annular body 19 which covers its end, in spite of the removed protective cover 5. The now emptied device can then be safely disposed of. The delivery device of the present invention can be advantageously used, not only for adding the desired volumes of liquid media to infusion containers, but can also be used equally for the delivery of liquid or gaseous and/or particle-laden media, to the extent their delivery by way of hypodermic needles is possible or necessary.

While an embodiment has been chosen to illustrate the invention, it will be understood by those skilled in the art that various changes and modifications can be made therein without departing from the scope of the invention as defined in the appended claims.

What is claimed is:

1. A device for distributing substances, comprising:
a delivery container holding a pertinent medium,
a closing unit on said delivery container and having a hypodermic needle for delivering said medium, said hypodermic needle having an outer end projecting out of said closing unit
a safety device having an annular body and being movably guided a section of said hypodermic needle projecting from said closing unit between an active protective state covering said outer end of said needle and an inactive state exposing said outer end for delivery of said medium from said hypodermic needle, said annular body being movable on said needle from said outer end of said needle in said active protective state to a position axially spaced from said outer end for delivery of said medium and vice versa, said annular body being connected to said closing unit and elastically biased toward said active protective state by elastic support elements divided by bending joints and articulated to said annular body and to said closing unit, said support elements being substantially parallel to said hypodermic needle in said active protective position and being spread out from said hypodermic needle in said inactive state, said support elements extending in one piece from said closing unit to said annular body and being divided at approximate half lengths thereof by said bending joints;
a snap ring removably mounted on said closing unit and movable along said support elements to said bending joints to lock said support elements in said active protective state; and
a protective cover removably coupled to said delivery container by a predetermined breakage point and enclosing said outer end of said hypodermic needle;
whereby said hypodermic needle can penetrate a perforable closure of a receiving container to deliver said medium into the receiving container, and whereby said annular body is pushed back from said active protective state to said inactive state by contact with the perforable closure.

2. A device according to claim 1 wherein
said protective cover has a finger-grip knob as purchase for twisting said protective cover off of said delivery container.

3. A device according to claim 1 wherein
said closing unit has a membrane located in said delivery container, facing an inner end of said hypodermic needle and forming a blocking element which can be pressed against and punctured by said inner end of said needle upon increasing pressure of said medium.

4. A device according to claim 3 wherein
said delivery container has a deformable wall and can be compressed to increase pressure of said medium in said delivery container.

5. A device according to claim 4 wherein
said deformable wall comprises a folding bellows.

6. A device according to claim 1 wherein
said bending joints have notches to engage said snap ring.

* * * * *